United States Patent
Harris et al.

(10) Patent No.: US 6,221,101 B1
(45) Date of Patent: Apr. 24, 2001

(54) CONTROLLED VORTEX INDUCING VASCULAR PROSTHESIS

(75) Inventors: Peter Lyon Harris; Thien Voon How, both of Liverpool (GB)

(73) Assignee: IMPRA, Inc., Tempe, AZ (US)

( * ) Notice: Subject to any disclaimer, the term of this patent is extended or adjusted under 35 U.S.C. 154(b) by 0 days.

(21) Appl. No.: 09/183,132

(22) Filed: Oct. 30, 1998

Related U.S. Application Data

(63) Continuation of application No. 08/656,065, filed on May 31, 1996, now Pat. No. 5,861,026.

(30) Foreign Application Priority Data

May 31, 1995 (GB) .................................................. 9510967

(51) Int. Cl.[7] ...................................................... A61F 2/00
(52) U.S. Cl. ........................................... 623/1.31; 623/1.1
(58) Field of Search ................................. 623/1, 2, 11, 12, 623/1.3, 1.31, 1.36, 1.37; 604/8, 14, 44

(56) References Cited

U.S. PATENT DOCUMENTS

| | | |
|---|---|---|
| 4,098,571 | 7/1978 | Miyata et al. . |
| 4,441,215 | 4/1984 | Kaster . |
| 4,503,568 | 3/1985 | Madras . |
| 4,530,113 | 7/1985 | Matterson . |
| 5,156,619 | 10/1992 | Ehrenfeld . |
| 5,443,497 | 8/1995 | Venbrux . |
| 5,456,714 | 10/1995 | Owen . |
| 5,472,404 | 12/1995 | Volgushev . |
| 5,500,014 | 3/1996 | Quijano et al. . |

*Primary Examiner*—Michael J. Milano
(74) *Attorney, Agent, or Firm*—Morrison & Foerster LLP; Todd W. Wight

(57) ABSTRACT

A vascular prosthesis comprising a tube of material other than autologous vascular tissue but considered/approved as safe and supple enough for use instead of such tissue, the tube having an end formation for surgical connection directly to an opening formed in an artery, the end formation serving to promote, at that end and/or within the direct connection and in response to normally pulsed blood flow, localized movement of blood having a non-laminar nature with a shear stress inducing relation to receiving arterial wall.

5 Claims, 1 Drawing Sheet

CONTROLLED VORTEX INDUCING VASCULAR PROSTHESIS

This is a continuation of application Ser. No. 08/656,065; filed on May 31, 1996, now U.S. Pat. No. 5,861,026, the entire disclosure of which is hereby incorporated by reference.

BACKGROUND OF THE INVENTION

1. Field of the Invention

This invention relates to aiding vascular surgery, including improving nature and use of prosthetic grafts, particularly for by-passes to relatively small arteries.

2. Description of Related Art

By-passes required to save limbs can be long even stretching from a groin to below a knee. The arteries to which by-passes are connected may be as small as one to five millimeter across. Where patients have no suitable veins to use as by-passes, which is often the case for patients with relevant serious conditions, the only positive alternative is use of prosthetic grafts made of synthetic materials, for such as flexible tube of PTFE (polytetrafluoroethylene). Justification would become questionable without reasonable success rates and/or improvement prospects. Making simple direct end connections or anastomoses of prosthetic graft tubes (usually run at an acute angle or more or less parallel with the artery and end cut at an angle) to side apertures in arteries, perhaps particulary arteries substantially less than five millimeters across, has been followed by such liability to fibrous intimal hyperplasia as later to lead to serious blood flow reduction, even stoppage. Such problems have led to various theoretical considerations and assumptions, including as backing to more complex practical proposals.

We are particularly familiar with one such practical proposal, namely use of a small piece of natural vein to make a short cuff that is joined by surgical stitching to and between the artery opening and the end of the prosthetic graft tube. Improved success rates for indirect prosthesis-to-vein-to-artery connection, compared with direct prosthesis-to-artery, have involved reduced adverse effect from intimal hyperplasia. Contributory factors, for cuff-type and other prosthesis types, have been considered and postulated as including reducing tendencies to turbulence of blood flow, and/or optimising approximation to laminar blood flow, and/or for suppleness of the natural vein parts to aid absorption or cushioning blood pulsing. These factors have further been seen particulary as contributing to avoiding or minimising occurrence of artery wall shear stress.

This invention has arisen from questioning such theorising and assumption, particulary after reflecting on the fact that success of autologous natural vein cuffs has included using cuff sizes so large as to make us doubt that either of laminar flow or pulse absorption would be likely to occur. Close observation of careful simulations has not only supported that view, but has further led us to develop successful proposals based on contradicting both of the prior objectives for maximising laminar flow and minimising artery wall shear stress.

BRIEF SUMMARY OF THE INVENTION

According to one aspect of this invention, there is provided a vascular prosthesis comprising a tube of material other than autologous vascular tissue but considered/ approved as safe and supple enough for use instead of such tissue; the tube of material having an end formation for surgical connection directly to an opening formed in an artery, said end formation serving to promote, at that end and/or within said direct connection, and in response to normally pulsed blood flow, localised movement of blood having a non-laminar nature with a shear stress inducing relationship to receiving arterial wall.

The term "non-laminar" as used herein is intended to define blood flow other than parallel to arterial walls and, in particular, includes localised laminar movement of blood having significant secondary components.

Separation of flowing blood from the inner wall of the tube near its said end, and associated with non-laminar flow, is preferable such as to produce a swirling action that may include locally circulatory or re-circulatory movement of blood, further preferably in the nature of or including a vortex action. Such blood flow separation will usually be at and adjacent to the end of the prosthesis tube which is acutely angled for connection to the artery. The blood flow separation is also preferably at least partially within an enlarging formation of the prostheses associated with said angled end of the prosthesis tube.

A preferred end formation of the prosthesis tube of the invention is an enlargement which produces a sudden expansion of the blood volume therein and hence an increase in the blood flow rate.

Desired non-laminar blood flow promotion is preferably effective only in phases of cycles of blood-flow pulsing, which phases preferably alternate with other phases of more laminar flow sufficient to assist flow of all blood into the artery away and from that end of the prosthesis. The pulsed nature of normal blood flow involves successive time-spaced rises in pressure. Each pressure rise preferably causes both an initial relatively smooth or laminar blood flow in and out of the prosthesis-to-artery connection and a later transition into desired non-laminar blood movement. The preferred non-laminar vortex type movement preferably collapses before the next pressure rise.

In our simulation of cuff-type of prior prosthesis graft connections to arteries, and modelling/prototyping for the specific embodiment of this invention to be described with reference to the accompanying drawings, we discovered and sought to develop and/or improve pronounced single vortex action as will become clear. In looking at other prior prostheses actually in use, such as the so-called Taylor Patch and/or St. Mary's Boot, we also observed definite though somewhat different non-laminar flows in and through the arterial connections involved, including two lesser relatively fore and aft vortex actions and a quite large turbulence that seems not to develop fully into clear vortex action. It now appears to us that the cuff-connections are effective mainly by reason of their geometry, leaving space for beneficial non-laminar blood movement, particulary clear vortex action as in the specific description to follow. It is further the case that the different non-laminar blood flows through other types of prosthesis graft tube ends in to arteries can also be reproduced by tube ends appropriately replicating significant features of arterial connection geometry described herein. It is a further aspect of this invention that any successful prior prostheses using autologous vein material or other compound structure be made with similar end-connection formations, but be of homogeneous wholly synthetic material for direct arterial connection.

According to another aspect of this invention, there is provided a vascular prothesis comprising a tube of material other than autologous vascular tissue but considered/ approved as safe and supple enough for use in substitution for such tissue, the tube of material having a relatively enlarged end for actual connection directly to an opening formed in an artery. Suitable said end enlargement can assure that pulsed blood flow from the prosthesis into the artery periodically separates from said material before and on its way out of the prosthesis. The resulting non-laminar blood flow appears to be generally beneficial, particularly, if not exclusively, if with a strong vortex action component or otherwise inducing shear stress in arterial walls.

Evolution and exemplary specific implementation will now be specifically described with reference to the accompanying diagrammatic drawings.

DETAILED DESCRIPTION OF THE INVENTION

Figure 1:
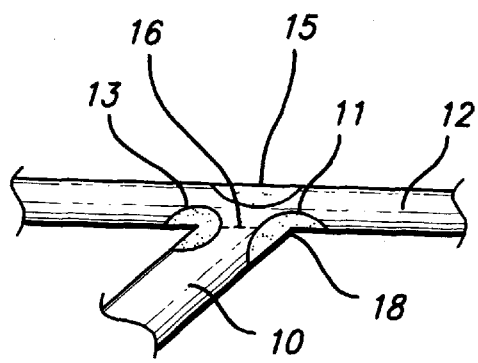
FIG. 1 is an idealised sectional line diagram useful for explaining problems arising for simple direct connection or anastomosis of a prosthetic graft tube 10 of synthetic material to an opening made in an artery 12.
Figure 2:
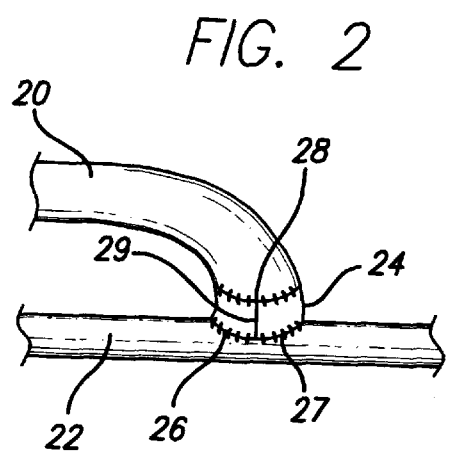
FIG. 2 is another sectional line diagram showing idealised use of a veinous cuff 24 interposed between a prosthetic graft tube 20 and an artery 22.

In the drawings, referring first to FIG. 1, artery 12 has an opening made by incision at 16. Prosthetic graft tube 10 of synthetic material (for which PTFE, most usually ePTFE, is widely used in practice and is our own current first choice material) is run at an acute angle or more or less parallel to the artery 12. Tube 10 is indicated cut to an angled end 18 that is end-to-edge sewn into the opening 16. Unfortunately, there is a tendency for myointimal hyperplasia to occur later in the receiving artery 12, see indicated development of fibrous or scar-like tissue at fore and aft, or toe and heel, positions 11 and 13, respectively, and also at plate position 15 opposite the opening 16. This development can seriously reduce the very blood flow that it is the object of the procedure to improve. Indeed, this condition all too often progresses to blocking such blood flow altogether. These problems are all the greater the smaller the calibre of the receiving vein 12, which can be as small as one to five millimeters for the sort of distal by-passes often needed, say to go from the groin to beyond the knee as frequently necessary to save the lower leg.

One prior proposal, known as the Miller Cuff, aimed at reducing such problems takes a short length of other vein, usually from still usable parts of the saphenous vein that would be used in its entirety if serviceable. This short length of autologous vein, typically two to three millimeters in diameter, is removed and opened along its length, then sutured first, see 27, to the opening 26 in the artery 22 and end-to-end to itself, see 29. The completed cuff 24 is trimmed and anastomosis completed, see 28 to normally wider prosthetic graft tube 20. The graft tube 20 is typically PTFE and is at least four millimeters, preferably six if not more, in diameter. Improvement in terms of reducing or avoiding development of intimal hyperplasia was originally, and has since consistently been, attributed to the autologous vein-to-artery junction. The suppleness of the veinous tissue may also have contributed to these improvements by assisting absorption of pressure pulsing and reducing shear wall stress in the receiving artery. Shear wall stress was assumed and reported as being the major causative factor in development of intimal hyperplasia. This procedure has become popular and has been the subject of considerable development, including to use in a compound manner relative to interconnected small arteries.

Figure 3:
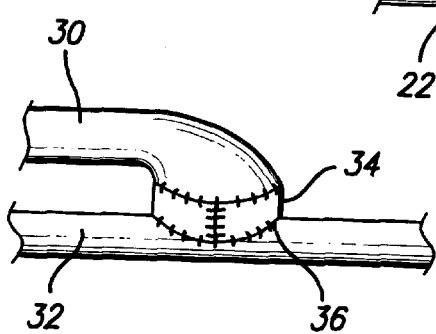
FIG. 3 is similar to FIG. 2 but showing a variant using a wider veinous cuff 34.

Turning to FIG. 3, a variant is shown that reduces significantly the surgical constraints imposed even by suturing at an artery aperture size matching the diameter of the prosthetic graft tube, typically six millimeters.

FIG. 3 shows a larger size of cuff 34, often much larger in practice, typically up to ten or twelve millimeters if not more in diameter, even for a six millimeter diameter tube 30. Formation of tucks in the. end of the cuff 34 to join to the end of the tube 30 can be avoided as ends of PTFE tubes are readily spread to match the cuff 34. This variant is found to be at least as effective as the original Miller Cuff proposal involving much closer matching of the diameters of the cuff (24) and the tube (20).

Simulative investigation of the FIG. 3 variant produced immediately surprising results, particularly in terms of finding a strong vortex action in the blood flow within the cuff 34, including extension into the artery 32 through the opening 36. It is, of course, inevitable that circulatory blood movement close to walls of the cuff and the receiving artery, particularly at their junction, must produce quite high shear wall stressing. Moreover, no clear indication was found of significant (or any) pressure pulse absorptive radial expanding and relaxing in the cuff. A radical possibility was thus considered, namely that development of myointimal hyperplasia might not only not be induced by shear wall stress, but actually being repressed by it.

Figure 4:
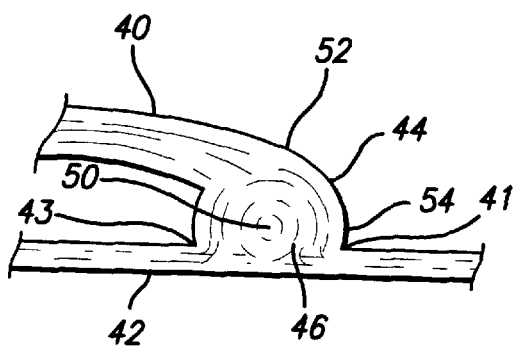
FIG. 4 is also a sectional line diagram but showing an embodiment of this invention as a prosthetic graft tube 40 with an enlarged end 44 for direct connection or anastomosis to an artery 42 and vortex action 46 within the junction.

Whether or not such postulation is true our further development work, see FIG. 4, has demonstrated success for simple enlargement 44 of the end of a prosthetic by-pass graft tube 40 of PTFE and its direct connection or anastomosis to an opening 46 in the receiving artery 42, such provision serving to emulate the space afforded in FIG. 3 and now occupied by vortex action 50 into and adjacent opening formed in the receiving artery 42. The enlargement 44 comprises a first part 52 of gradually increasing diameter and a second part 54 for connection to the arterial wall of ring-shape with a convex outer wall. Indeed, smoother transitions in the tube end 44, compared with suturing to a specific veinous cuff, are believed to be advantageous—quite apart from the very substantial savings of work and time naturally following from need for only a single suturing stage.

As there is usually no significant problem with making direct connections or anastomoses of prosthetic tube to by-pass supplying arteries, which are usually of much larger calibre, we envisage supply of such tube with one enlarged end, perhaps both, then with a choice of which end to use and which to trim to length. Alternatives include specific purpose-made tube-end-components for attachment to simple tube, feasibly other than by suturing, say by adhesive or welding, and capable of being done as separate from actual surgical operations.

Returning to illustration for the embodiment of this invention being specifically described, the vortex action can be seen extending into the receiving artery 42, and we believe this could be important. Also, the overall cuff-and-artery containing space for the vortex action 50 is shown greater than such action itself. Blood flow is permitted into the receiving artery 42 past vortex 50 and the toe 41 of the prosthetic anastomosis in one direction and at least off the bottom of the vortex 50 (and/or past its other side, though not always visible in simulations to date and perhaps possible or best to be avoided) and the heel 43 in the opposite direction.

Figure 5:
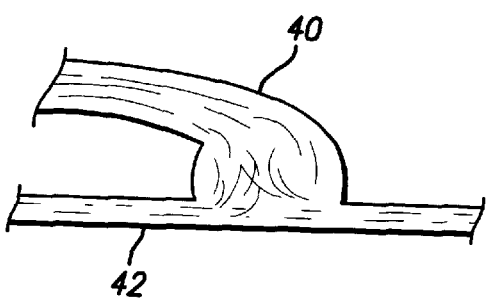
FIG. 5 is as FIG. 4 but showing flow free of the vortex action.
Figure 6:
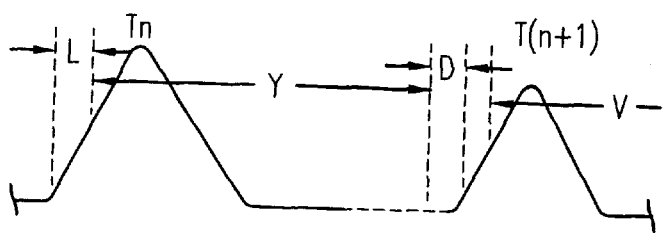
FIG. 6 is a line diagram indicating two successive blood pressure pulses T(n) and T(n+1).

Moreover, appropriate sizing and shaping of the end 44 of the prosthetic tube 40, thus the space containing the vortex action 50, will assure not only induction of that vortex action 50 during rise of each blood pressure pulse along with adequate blood flow around or past or off it, but also collapse of such vortex action 50 at or before rise of the next blood pressure pulse and an immediate response to the latter, see FIG. 5, by way of initial much smoother and nearer to laminar flow before re-start of the vortex action 50. This cyclic multi-phase action is indicated in FIG. 6 for consecutive blood pressure pulses T(n) and T(n+1) with V representing vortex action 50 starting as a phase within the rise of each blood pressure pulse, and L representing smoother nearer laminar blood flow in preceding phase in the rise of each blood pressure pulse and before onset of vortex action 50. The interval or phase L and its non-vortex action flow assures that there is no tendency for blood that becomes static in preceding phase V of the vortex action 50 (which is rather more complex than indicated by the side-on observation of actual circulatory and re-circulatory movement concentrated upon in FIG. 4) to remain uncleared. Another interval or phase is indicated at D in FIG. 6 as corresponding to collapse of the circulatory and re-circulatory vortex action component 50 before the next blood pressure pulse rise. Detailed design of the prosthesis tube end may afford a means for controlling the interval or phase D in desirable ways assuring full collapse of the vortex action 50. It is feasible for the strength and normal intervals of individual patients' heart beat rate to be catered for by a range of sizes and/or shapes of prosthetic tube endings.

Finally, our simulations of actual blood flows through other by-pass prostheses and into receiving arteries, including the well-know Taylor Patch and St. Mary's Boot, has indicated substantially similarly cyclically repeating phases of intercalated highly non-laminar and relatively smoother and more laminar blood flows, including with mainly both of smaller toe-adjacent and heel-adjacent vortex actions and a turbulence short of vortex induction. Such alternative by-pass prosthetic provisions being in use successfully, it is further proposed herein, as alternative embodiments of this invention, that geometry of prosthetic tube ends be designed to emulate such flows or induce flows with similarly effective results as successful by-pass prosthetic devices.

We claim:

1. A vascular prosthesis comprising:
    an expanded polytetrafluoroethylene tube having a first and second end;
    an enlarged chamber of expanded polytetrafluoroethylene, continuous and integral to the first end of the tube without sutures associated therewith, wherein the enlarged chamber is configured to promote localized non-laminar movement of blood.

2. A vascular prosthesis as in claim 1, further comprising a second enlarged chamber of expanded polytetrafluoroethylene, continuous and integral to the second end of the tube without stitches associated therewith, wherein the second enlarged chamber is configured to promote localized non-laminar movement of blood.

3. A vascular prosthesis as in claim 1, wherein the enlarged chamber is adapted to be connected to an artery with a diameter in the range of 1 to 5 mm.

4. A vascular prosthesis as in claim 1, wherein the enlarged chamber is adapted to be connected to an artery without the use of sutures.

5. A vascular prosthesis as in claim 1, wherein the non-laminar movement of blood comprises a controlled vortex through the enlarged chamber and into an artery connected thereto.

\* \* \* \* \*